United States Patent [19]

Zhong et al.

[11] Patent Number: 5,800,365
[45] Date of Patent: Sep. 1, 1998

[54] MICROSECOND TANDEM-PULSE ELECTROHYDRAULIC SHOCK WAVE GENERATOR WITH CONFOCAL REFLECTORS

[75] Inventors: Pei Zhong; Franklin H. Cocks, both of Durham; Glenn M. Preminger, Chapel Hill, all of N.C.

[73] Assignee: Duke University, Durham, N.C.

[21] Appl. No.: 572,305

[22] Filed: Dec. 14, 1995

[51] Int. Cl.⁶ .................................. A61B 17/22
[52] U.S. Cl. .................................... 601/4
[58] Field of Search .............. 128/660.03; 601/2–4; 600/439

[56] References Cited

U.S. PATENT DOCUMENTS

| | | | |
|---|---|---|---|
| 3,942,531 | 3/1976 | Gunter et al. | 128/328 |
| 4,655,220 | 4/1987 | Hahn et al. | 128/328 |
| 4,664,111 | 5/1987 | Reichenberger | 128/328 |
| 4,821,730 | 4/1989 | Wurster et al. | 128/660.03 |
| 4,888,746 | 12/1989 | Wurster et al. | 367/138 |
| 4,889,122 | 12/1989 | Watmough et al. | 601/3 |
| 5,143,073 | 9/1992 | Dory | 601/2 |
| 5,209,221 | 5/1993 | Riedlinger | 128/24 AA |
| 5,224,468 | 7/1993 | Grüwald et al. | 601/4 |
| 5,229,401 | 7/1993 | Cathignol et al. | 128/660.03 |
| 5,582,578 | 12/1996 | Zhong et al. | 601/2 |

Primary Examiner—Brian L. Caster

[57] ABSTRACT

The invention discloses a microsecond tandem-pulse electrohydraulic shock wave generator for the comminution of concretions in vivo by controlled, concentrated cavitation energy. This apparatus generates a primary and a secondary shock wave pulse with a specified time delay in microseconds and pressure relationships, with the primary shock wave pulse being used to induce a transient cavitation bubble cluster near the target concretion, and the secondary shock wave pulse consisting of a sequence of reflected pulses producing a pulse that is substantially compressive to control and force the collapse of the cavitation bubble cluster towards the target concretion. This microsecond tandem-pulse is produced by the use of a plurality of ellipsoidal reflecting surfaces of the same focal length, but different major and minor axes. These two microsecond shock wave pulses, one having a compressive and a tensile component and one having essentially only a compressive component have been found to give concentrated energy deposition on the target concretion, while avoiding injury to surrounding tissue caused by random collapse of the cavitation bubbles, thus enhancing the efficiency of fragmentation of the concretion using shock waves while reducing potential deleterious injury to surrounding tissue.

7 Claims, 3 Drawing Sheets

MICROSECOND TANDEM-PULSE ELECTROHYDRAULIC SHOCK WAVE GENERATOR WITH CONFOCAL REFLECTORS

FIELD OF THE INVENTION

The present invention is a microsecond tandem-pulse electrohydraulic shock wave generator, with at least two truncated, ellipsoidal reflecting surfaces having the same foci, for disintegration of concretions in vivo with reduced tissue injury by the forced concentration of acoustically induced transient cavitation energy towards the target concretions, by means of dual pulses of controlled time sequence and controlled compressive/tensile stress ratios.

BACKGROUND OF THE INVENTION

Comminution of concretions in vivo using extracorporeally generated shock waves (lithotripsy) is a wide-spread medical practice in the treatment of urinary stone and biliary stone disease. Prior art describes various devices and methods for generating high-intensity, focused shock waves for the fragmentation of concretions inside a human being. U.S. Pat. No. 3,942,531 by Hoff, et al. discloses the use of a spark gap discharge in water to generate a shock wave within an ellipsoidal reflector which couples and focuses the shock wave to fragment kidney stones inside the body. Hahn, et al. in U.S. Pat. No. 4,655,220 disclose a device using a coil and a mating radiator, in the form of spherical segment, to produce magnetically induced self-converging shock waves. Wurster, et al. in U.S. Pat. Nos. 4,821,730 and 4,888,746, disclose the use of piezoelectric elements arranged in mosaic form on a spheroidal cap to produce focused high-intensity shock waves at the geometric center of the cap, where the concretion must be placed.

Despite the different principles used for shock wave generation, all of these devices produce shock waves of a similar waveform, which can be characterized by a compressive phase consisting of a rapid shock front with a positive peak pressure up to 100 mega pascals (MPa), followed by a tensile (negative) phase with a negative peak pressure up to 10 MPa and with an overall total duration of a few microseconds. It is also well known in the art that the negative phase of an incident shock wave can induce transient cavitation bubbles in the focal region, if the peak amplitude of this tensile stress exceeds about 1 MPa.

It is further known in the art that when cavitation bubbles collapse near a stone surface, microjets will be produced due to the asymmetric collapse of these cavitation bubbles. Some of the microjets impinge violently onto the stone surface and cause stone fragmentation. Experiments have shown that using the same shock wave generator at the same intensity level, a stone immersed in glycerol (a cavitation inhibitive medium) will not be damaged, while the same stone immersed in water (a cavitation promotive medium) can be fragmented, despite the fact that the shock wave energy in both cases is very nearly the same. It is now established in the art that shock wave induced cavitation and the resultant microjet impingement is the primary mechanism for stone fragmentation. Furthermore, when shock wave-induced cavitation bubbles collapse near tissue surfaces, they can cause tissue injury through shock wave emission, the generation of high-temperatures, microjets, and the shear stresses associated with rapid bubble oscillation.

The present invention is based upon the discovery that the collapse of a cavitation bubble cluster can be controlled so as to cause increased concretion comminution by imposing an impinging, secondary compressive or substantially compressive shock wave to collapse the bubble cluster from its outer layer into an inner layer collectively. This secondary shock wave pulse is preferably of relatively long duration compared to the tensile phase of the primary shock wave pulse, and is directed confocally with the first pulse, but has a small, or no, tensile component to ensure that this secondary shock wave pulse leads to complete collapse of the cavitation bubble cluster, while not itself inducing cavitation.

By directing the impinging shock wave in the direction of the concretions to be comminuted, it has now been discovered that the resultant comminution is greatly enhanced over that comminution which occurs when cavitation bubbles collapse in an uncontrolled and unforced manner. Furthermore, the collapse of a cavitation bubble by an impinging shock wave has been found to be asymmetric, leading to the formation of a liquid jet which travels along the direction of the impinging shock wave. When occurring in water the liquid jet will be a water jet. It has been discovered that the collapse of a cavitation bubble can be controlled and guided by an incident shock wave, provided that this shock wave is applied at the correct time in the life of a cavitation bubble and is preferably of a relatively long duration so that the majority of cavitation bubbles are affected. It has now been found that the forced collapse of a cavitation bubble cluster by an impinging shock wave can concentrate 80% to 90% of the cavitation bubble cluster energy towards the center of the cavitation bubble cluster where the target concretion is placed. This concerted, controlled collapse of a cavitation bubble cluster by an impinging shock wave has been found to produce a concentration of the cavitation energy towards the concretion. Because the cavitation energy is directed towards and concentrated on the target concretion, tissue injury associated with the comminution of the concretion is reduced.

Riedlinger, in U.S. Pat. No. 5,209,221, discloses a device for generating sonic signals for limiting, preventing or regressing the growth of pathological tissue in vivo. The sonic signal, consisting of at least one rarefaction phase with a negative sonic pressure amplitude with a value greater than $2 \times 10^5$ Pa, is radiated with a carrier frequency exceeding 20 kHz, a sonic pulse duration, T, of less than 100 microseconds and a pulse recurrence rate of less than $1/(5T)$. Thus, the time delay between two adjacent sonic pulses is greater than 500 microseconds. Since experiments have shown that the transient cavitation bubble clusters generated by all current lithotripsy devices last less than 400 microseconds, it is clear that by using the sonic pulse sequence as disclosed by Riedlinger, the ensuing sonic pulses will not be able to control the collapse of the cavitation bubble cluster induced by the initial sonic pulse.

Similarly, Cathignol, et al. in U.S. Pat. No. 5,219,401 disclose an apparatus for the selective destruction of biological materials, including cells, soft tissues, and bones. The injection of gas bubble precursor microcapsules, having diameters preferably in the 0.5 to 300 microns range and made from materials such as lecithin, into the blood stream is used by Cathignol, et al. as the primary means of generating gas bubbles in vivo. Although the phenomenon of cavitation provoked by an ultrasonic wave generator working in a frequency range of $10^4$ to $10^5$ Hz is described, the sonic pulse sequence is not specified. As we have now discovered, the forced collapse of cavitation bubbles to produce fluid microjets for the enhanced comminution of concretions requires a specified relationship between the first, cavitation-inducing, acoustic pulse and the second, cavitation-collapsing, acoustic pulse. In addition, we have now also discovered that the second, cavitation-collapsing, acoustic pulse must have a compressive (positive) phase with a relative long duration and only a small, or no, tensile (negative) component.

Reichenberger, in U.S. Pat. No. 4,664,111, discloses a shock wave tube for generating time-staggered shock waves by means of a splitting device, such as a cone, for the fragmentation of concrements in vivo. Reichenberger discloses that the effects of the shock waves can be improved if they are so closely spaced in time that they overlap in their action on the concrement. The effects of shock wave induced cavitation are not disclosed by Reichenberger.

None of the prior art teaches the use of a secondary, substantially compressive shock wave, imposed at a specified time delay, to control the collapse of a transient cavitation bubble cluster induced by a primary shock wave. Without this time sequenced secondary shock wave, the efficiency of comminuting concretions in vivo by shock wave lithotripsy will be relatively low, and even though comminution can be produced finally by the application of thousands of shocks, the concomitant risk for tissue injury due to the uncontrolled cavitation energy deposition during the procedure will be concomitantly high.

In presently disclosed point source spark gap (electrohydraulic), electromagnetic, and piezoelectric shock wave generators, cavitation bubbles are formed after the passage of the incident shock wave. Furthermore, the shock wave-induced cavitation bubble clusters have been found to be extremely transient, lasting for less than 400 microseconds, a time much shorter than the interval of shock wave delivery, which is typically linked to the patient's heart-beat rate. Therefore, in presently used lithotripsy devices the collapse of the transient cavitation bubble cluster occurs in an uncontrolled, random fashion, and as a result only a small portion of the collapsing energy, typically less than 10%, is transmitted towards the stone surface, and the majority of the cavitation energy is either dissipated or absorbed by surrounding tissue. Consequently, large numbers of shock waves are needed for adequate stone fragmentation, and as a consequence concomitant tissue injury is also produced by current shock wave generators. Using current lithotripsy devices, more than 4,000 pulses may be needed in some cases to produce desired stone comminution, and significant tissue damage such as renal hemorrhage may accompany this process.

The prior art uses uncontrolled, shock wave-induced cavitation for the fragmentation of concretions in vivo. Because cavitation bubble collapse is uncontrolled in devices disclosed by the prior art, the fragmentation efficiency is low, and thus the number of required acoustic pulses for producing adequate stone comminution is high. Furthermore, the method and apparatus of the prior art has a high risk for tissue injury due to the random deposition of the cavitation energy to adjacent tissue when the cavitation bubbles collapse.

While it is not known with certainty why high intensity shock wave pulses reflected from ellipsoidal reflecting surfaces have a tensile component, it has been thought that such a tensile component can arise from acoustic diffraction which occurs at the aperture of the reflecting surface. We have discovered, however, that the installation of an acoustic blocking material to intercept such aperture diffractions still leaves a large tensile component to the shock wave observed at the second focus. Furthermore, we have found that when this acoustic absorbing material is placed in line with and perpendicular to the central axis of the ellipsoidal reflector, the tensile component of the shock wave is reduced, even though the absorbing material does not extend to the aperture. This result could not be due to aperture diffraction. Thus, it is not known with certainty why the tensile portion of the acoustic shock wave occurs. Even though the reasons for the existence of this tensile component are not known, we have now discovered that this tensile component can be reduced either by reducing the area of the reflecting surface so that both the tensile and the compressive components are reduced or by staggering the time delays of a series of reflected pulses such that the large compressive component of a later pulse overlays the tensile component of an earlier pulse, resulting in a substantially compressive-only ensemble of pulses, which taken together constitute the secondary shock wave pulse.

By combining a large primary reflecting surface with either one small reflecting surface or an ensemble of small reflecting surfaces of particular relative geometry, it has been found possible to produce a primary shock wave with a large compressive component and a smaller but still large tensile component and then to collapse the cavitation bubbles formed by the tensile component of this primary wave by the compressive component of an ensuing secondary wave, or ensemble of secondary waves that themselves do not induce cavitation.

PHYSICS OF THE METHOD

Any ellipse can be represented by the equation $$x^2/a^2 + y^2/b^2 = 1 \qquad \text{Eq. 1}$$

where $2a$ is the major axis, that is the distance from one end of the ellipse to the other as measured along the x axis which is taken as the long axis and where $2b$ is the minor axis of the ellipse as measured from one end to the other along the y axis, where a is greater than b. The rotation of this ellipse about the x-axis produces a so-called ellipse of revolution or an ellipsoid. Every ellipse will also have two foci, whose location on the axis where $2a$ is the major axis will be on the x-axis at +c and −c where $$c = (a^2 - b^2)^{1/2} \qquad \text{Eq.2}$$

As is well known, an expanding spherically divergent wave that originates at the first focal point will be reflected from the surface of the ellipse of revolution and will be redirected to the second focal point. The portion that will be so directed from a truncated ellipse of revolution is given by that portion of the total spherical wave which intercepts the truncated ellipsoid. Thus, as the area of a truncated ellipse of revolution decreases, so too will the fraction of the intercepted spherically divergent wave.

The time, t, required for any spherically divergent wave reflected from the inner surface of an ellipse of revolution to travel from the first focus to the second focus is given by $$t = 2a/s \qquad \text{Eq.3}$$

where s is the speed of the wave in the medium through which it is propagating. For an acoustic wave in water, s is approximately 1,500 meters per second. Thus, for an ellipse for which a is equal to 18 centimeters, this time will be about 240 microseconds. From Eq. 1 and Eq. 2, it can be see that c may be held fixed and constant while both a and b vary, provided that the difference $a^2 - b^2$ remains constant. Thus, it has been found possible to construct a nested set of truncated ellipses of revolution such that all ellipsoids share common foci but each can have a different major axis 2a. The eccentricity of an ellipse, e, is measured by the ratio c/a. Thus, ellipses which are nearly spherical will have an eccentricity nearly unity while ellipses which are increasingly elongated will have an eccentricity increasingly less than unity. Thus, for a fixed value of c, in order to have a greater value of a, it is necessary that the eccentricity of the ellipse decreases.

In the present case, we have discovered that for ellipses of revolution for which a is between 10 and 20 centimeters, it has been found to be necessary for a secondary, substantially compressive (tensile component less than 1 MPa) wave to follow within 20 to 400 microseconds of the primary wave, which has a tensile component greater than 1 MPa, so that the cavitation bubbles induced by the primary wave will be forced to collapse by the secondary wave. In order to achieve this time delay, the value of the major axis, $2a_2$, of the secondary truncated ellipse of revolution which reflects the secondary wave must be 30 to 600 millimeters longer than the major axis of the primary ellipse of revolution, $2a_1$.

If the area of the secondary truncated ellipsoid is increasingly made smaller, it has now been found that the tensile component of the secondary wave can be reduced below 1 MPa while the compressive component remains above 1 MPa. To increase the ratio of the compressive component of the secondary wave to the tensile component of the secondary wave we have now discovered that a plurality of secondary truncated ellipses of revolution can be used, where all truncated ellipsoids share common foci. If the primary truncated ellipse of revolution is denoted by the major and minor axes $2a_1$ and $2b_1$, respectively, then the secondary truncated ellipse of revolution can be denoted by $2a_n$ and $2b_n$, where n is an integer greater than 1 and n−1 is the total number of secondary truncated ellipses of revolution and $a_n$ is greater than $a_{n-1}$. The time delay, $\Delta t_n$, between the secondary shock wave pulses from truncated ellipses of revolution n and n−1, can then be calculated from $$\Delta t_n = 2(a_n - a_{n-1})/a \qquad \text{Eq. 4}$$

We have now discovered that $\Delta t_n$ should be between 0.5 to 5 microseconds, and thus $a_n - a_{n-1}$ should be between 0.375 and 3.75 millimeters, when c is between 6 and 18 centimeters and $2a_1$ is between 20 and 40 centimeters. The values of 0.5 to 5 microseconds have been discovered to produce an overlap of secondary pulses such that the compressive component of the shock wave pulse from the secondary truncated ellipse of revolution having a major axis $2a_n$ will overlay the tensile component of the shock wave pulse from the truncated ellipse of revolution having the major axis $2a_{n-1}$. In this way, we have now discovered that the resultant secondary shock wave can be made from an ensemble of pulses which have in total almost only a compressive character and of relatively long duration, typically 2 to 20 microseconds.

SUMMARY AND OBJECTIVES OF THE INVENTION

The present invention provides a microsecond tandem-pulse shock wave generator for producing a sequence of paired shock wave pulses with a specified very short time delay (less than 400 microseconds) between the tandem, paired pulses, and with pressure relationships between these pulses that provide both a means of inducing a transient cavitation cluster and a means of controlling the growth and subsequent collapse of the cavitation bubble cluster near the target concretions in vivo, to achieve increased fragmentation efficiency with reduced tissue injury.

It is an objective of the present invention to provide a microsecond tandem-pulse shock wave generator for producing the controlled, concentrated collapse of cavitation bubbles for effective comminution of concretions in vivo with reduced injury to surrounding tissue.

A further objective of the present invention is to produce controlled, concentrated cavitation bubble collapse by using a sequence of shock wave pulses with a specified time delay and with specified pressure relationships between the sequential shock wave pulses. The initial shock wave pulse induces a transient cavitation bubble cluster near the target concretion, while the subsequent shock wave pulse, which itself may be formed by the superposition of a number of pulses, forces and controls the collapse of the cavitation bubble cluster towards the target concretions in vivo.

It is still another objective of the present invention to use shock wave pulses propagating along different pathways through interposed living tissue before converging at the target concretion to minimize cavitation-induced tissue injury along the shock wave pathway while maximizing the shock wave-bubble interaction at the target concretion for improved comminution efficiency with reduced tissue injury.

It is yet another objective of the present invention to provide a means for the production of two, tandem, paired shock wave pulses, a primary pulse and a secondary pulse, in which the secondary pulse is itself a composite of multiple subsidiary pulses all from a single electric discharge, with these two shock wave pulses, primary and secondary, being separated in arrival time at their common focus by a fixed and known time delay.

It is still yet another objective of the present invention to reduce the magnitude of the tensile component of the secondary shock wave pulse by the superposition of a multiplicity of shock wave pulses each with a time delay such that the compressive component of a later pulse coincides with the tensile component of an earlier pulse to yield in their superposition a pulse of a relatively long compressive phase, but with little or no tensile component.

BRIEF DESCRIPTION OF THE DRAWINGS

The objectives and features of the present invention will become apparent from the following description and appended claims taken in conjunction with the accompanying drawings.

DETAILED DESCRIPTION OF THE PREFERRED EMBODIMENTS

Figure 1:
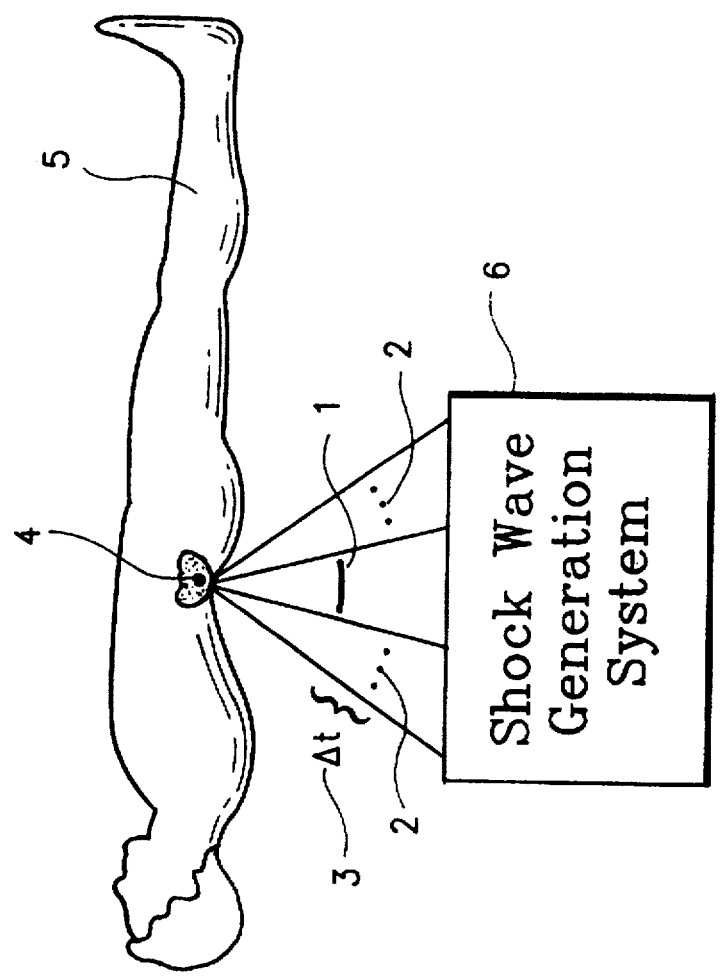
FIG. 1 shows a concretion in a living body and a shock wave generation system for generating two shock wave pulses, a primary pulse and a secondary pulse, in sequence and separated by a specified time delay and propagating coaxially along different pathways through interposed tissue in a living body before converging at the target concretion, for the comminution of concretions inside a living body.

According to a first preferred embodiment of the present invention, FIG. 1 shows a shock wave generation system for generating a primary shock wave pulse, 1, and a secondary shock wave pulse, 2, separated by a specified time delay $\Delta t$ 3 with respect to the primary pulse. The primary and the secondary shock wave pulses 1, 2 are produced by a shock wave generation system 6 and are aimed confocally at a common focal volume encompassing a target concretion 4 inside a living being 5, for the comminution of the target concretion 4 with improved fragmentation efficiency and reduced tissue injury. We have now discovered that for optimal effect, this time delay between the primary and the secondary pulse should be 20 to 400 microseconds (μs), when the major axis of the primary reflecting surface is 20 to 40 centimeters in length and the acoustic medium is water.

Figure 2:
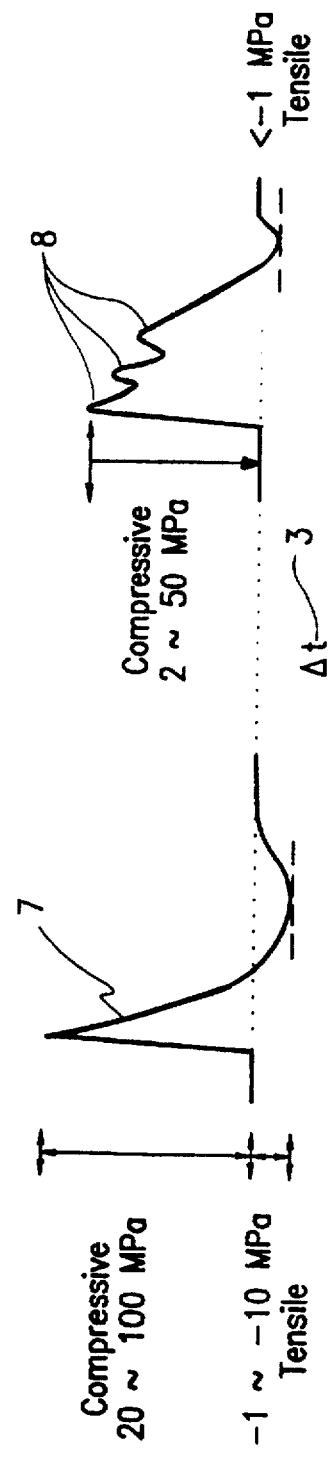
FIG. 2 shows two shock wave pulses in sequence separated by a specified time delay of 20 to 400 microseconds (μs) to induce, by the tensile phase of the first shock wave pulse, a transient acoustic cavitation bubble cluster near a target concretion and, as it has now been discovered, to collapse, by the secondary shock wave pulse, this induced cavitation bubble cluster after it expands to approximately its maximum size, in order to concentrate the cavitation energy in the form of liquid microjets impinging towards the target concretion for improved fragmentation efficiency with reduced tissue injury.
Figure 2:
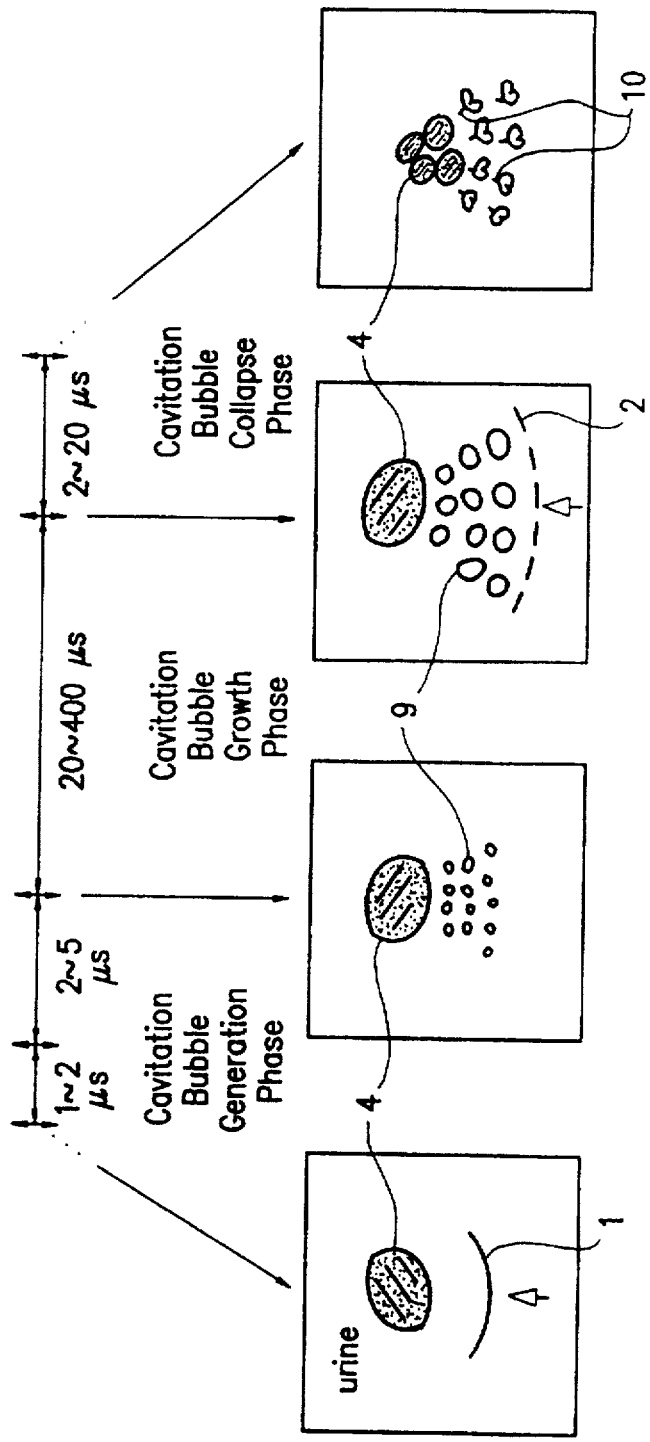

According to another preferred embodiment of the present invention as illustrated in FIG. 2, the pressure waveform 7 of the primary shock wave pulse 1 consists of a compressive phase with a positive peak pressure amplitude in the 20 to 100 MPa range and with a positive duration of 1 to 2 microseconds, followed by a tensile phase with a negative peak pressure amplitude of minus 1 to minus 10 MPa and with a duration of 2 to 5 microseconds. The pressure waveform 8 of the secondary shock wave pulse, 2, preferably consists of a series of compressive phases with reduced positive peak pressure amplitudes of 2 to 50 MPa and a total duration of 2 to 20 microseconds, and a small tensile phase with negative peak pressure less than minus 1 MPa. The tensile component of the secondary shock wave is reduced due to the superposition of the compressive component of a later secondary pulse overlapping the tensile component of an earlier secondary pulse. It has now been discovered that the time delay $\Delta t$ 3 between the primary shock wave pulse 1 and the secondary shock wave pulse 2 should be in a range of 20 to 400 microseconds when the major axis of the primary reflecting surface is 20 to 40 centimeters in length, and the time delay between each secondary pulses should be 0.5 to 5 microseconds from each other and that the total secondary pulse be substantially compressive and of 2 to 20 microseconds in total duration.

According to another embodiment of the present invention as shown in FIG. 2, the tensile phase of the primary shock wave pulse 1 is used to induce a transient cavitation bubble cluster 9 near a concretion 4, with the induced cavitation bubble cluster 9 growing to its maximum size in 20 to 400 microseconds, depending on the intensity of the primary shock wave pulse 1. The secondary shock wave pulse 2, separated from the primary shock wave pulse 1 by a specified time delay is used to collapse the cavitation bubble cluster 9 at or near its maximum expansion. If this secondary shock wave is also directed towards the target concretions, it has now been discovered that a concerted collapse of the cavitation bubble cluster 9 towards this target concretion 4 will occur. This forced, concerted collapse has now also been found to result in the formation of high-speed liquid jets 10 impinging towards the target concretion 4 and to cause disintegration of the stone 4 with increased rapidity as compared to the uncontrolled collapse of the cavitation bubble cluster. To ensure a complete collapse of the cavitation bubbles, the duration of the secondary pulse should be preferably at least 2 microseconds and preferably longer, up to 20 microseconds.

Figure 3:
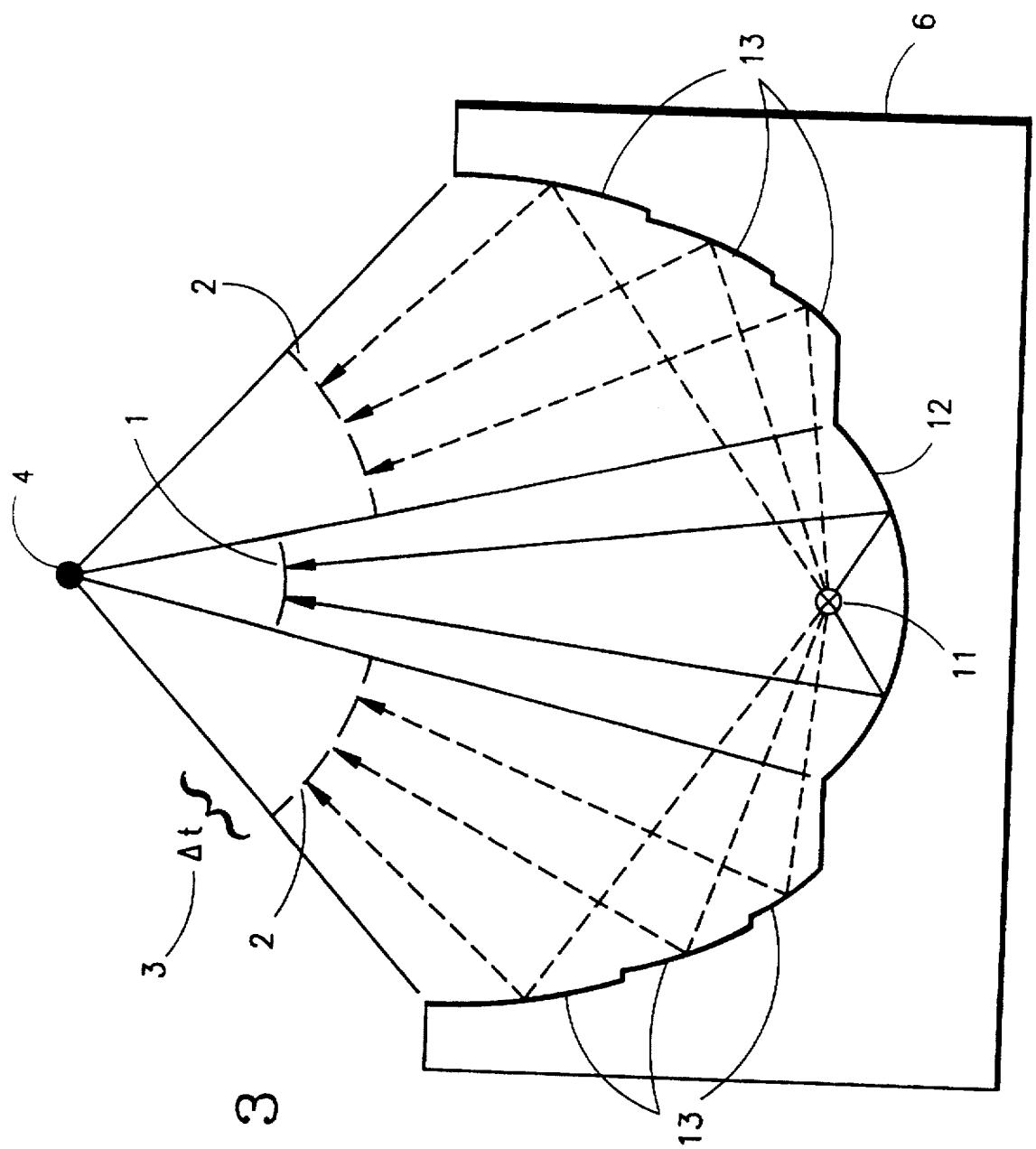
FIG. 3 shows a tandem shock wave generation system, consisting of a point shock wave source and a section of truncated ellipsoid acting as a primary reflecting surface, together with a plurality of secondary ellipsoidal reflecting surfaces having the same foci, for generating two shock wave pulses in sequence separated by a specified time delay and propagating coaxially along different pathways before converging at a common focal point where the target concretion is located.

According to a preferred embodiment of the present invention as shown in FIG. 3, the primary and the secondary shock wave pulses 1, 2 are produced by a shock wave generation system 6 consisting of a point shock wave source 11 for producing a spherically divergent shock wave pulse and a primary ellipsoidal reflecting surface 12 having a major axis, $2a_1$, a minor axis, $2b_1$, a focal length $2c_1$, and an eccentricity $e_1$, which reflects a primary portion of the spherically divergent shock wave pulse, and a secondary reflecting surface 13 consisting of a plurality of n truncated ellipsoidal reflecting surfaces, each having a major axis, $2a_n$, a minor axis $2b_n$, a focal length $2c_n$, and an eccentricities $e_n$, where n is an integer greater than 1, and the secondary reflecting surface 13 reflects a secondary portion of the spherically divergent shock wave pulse. If there is only one secondary reflecting surface, its major axis will have the length $2a_2$, its minor axis will have the length $2b_2$, and its focal length and eccentricity will be $2c_2$ and $e_2$, respectively. The point shock wave source 11 can be an electrohydraulic device, utilizing a spark gap discharge in water, such as disclosed by Hoff, et al in U.S. Pat. No. 3,942,531. It has now been discovered that the primary truncated ellipsoidal reflecting surface, 12, and each of the truncated ellipsoidal reflecting surface in the secondary reflecting surface, 13, must be constructed in such a way that they share common first and second focal points, that is $c_1$ is equal to $c_n$, and that the first focal point coincides with the point shock wave source 11 and the second focal point coincides with the target concretion 4. If the major axis of each of the secondary ellipsoidal reflecting surface, $2a_n$, is greater than the major axis of the primary ellipsoidal reflector, $2a_1$, then, the arrival of the primary shock wave pulse 1 and each of the secondary shock wave pulses in the secondary shock wave 2 at the target concretion 4 will be separated in time by a primary time delay $\Delta t$ 3. This primary time delay $\Delta t$ 3 can be calculated from two times $(a_n - a_1)$ divided by the acoustic wave speed in water. Each truncated ellipsoidal reflecting surface in the secondary reflecting surface, 13, is separated from every other by a secondary time delay, which can be similarly calculated from the difference in the major axes of the adjacent ellipsoidal surfaces used to produce the aggregate secondary pulse. We have now discovered that for optimal effect, $2a_n$ should be 30 to 600 millimeters longer than $2a_1$, and $2a_n$ should be 0.75 to 7.5 millimeters longer than $2a_{n-1}$ corresponding to a primary time delay of 20 to 400 microseconds and a secondary time delay of 0.5 to 5 microseconds, respectively, for acoustic pulses produced in water, and the eccentricity $e_1$ must be greater than the eccentricity $e_n$, and eccentricity $e_{n-1}$ must be greater than the eccentricity $e_n$, where $2a_1$ is between 20 and 40 centimeters in length.

It is well known in the art that with current lithotripters the beam diameter of the primary shock wave pulse 1 in the focal plane and the depth of focus along the shock wave axis are in the range of 2 to 15, and 12 to 120 millimeters, respectively. It has now been discovered that the transient cavitation bubble cluster, induced by the primary shock wave pulse 1, is distributed in a volume between 1.4 and 65 cubic centimeters, when $a_1$ is between 10 and 20 centimeters in length and the eccentricity of the primary reflecting surface is between 0.6 and 0.9.

According to still another advantageous embodiment of the present invention as shown schematically in FIGS. 1 and 3, the primary shock wave pulse 1 and the secondary shock wave pulse 2 generated by the shock wave generation system 6 are sent in such a configuration that these shock wave pulses 1, 2 propagate along different pathways in the interposed tissue before arriving at the target concretion 4. Thus these two shock wave pulses have a common second focus, and this focus is at or near the target concretion 4. A particular advantage of this embodiment is that the primary shock wave pulse 1 and the secondary shock wave pulse 2, which can be an ensemble of shock wave pulse or a single pulse with reduced tensile component, will not interact with each other along the interposed tissue pathway. Therefore, intensive shock wave-cavitation bubble interaction will not occur in the interposed tissue along the shock wave pathways, but will be produced at or near the target concretion 4.

It will be obvious to those skilled in the art that many modifications may be made within the scope of the present invention without departing from the spirit thereof. The present apparatus may be applied to the treatment of ureteral stones, bladder stone, gallstones, and other concretions located within a living body in addition to kidney stones.

We claim:

1. A microsecond tandem-pulse shock wave generator for comminuting, with reduced tissue injury, concretions in vivo, said microsecond tandem-pulse shock wave generator generating a primary shock wave pulse and also generating a secondary shock wave pulse separated in time from said primary shock wave pulse by a time delay with respect to said primary shock wave pulse, said microsecond tandem-pulse shock wave generator comprising:

a point shock wave source for producing a spherically divergent shock wave pulse, having a speed in water, s, and;

a primary truncated ellipsoidal reflecting surface having a major axis, $2a_1$, a minor axis, $2b_1$, a focal length $2c_1$, and an eccentricity $e_1$, said primary reflecting surface reflecting a primary portion of said spherically divergent shock wave pulse, and;

a secondary reflecting surface having at least one truncated ellipsoidal reflecting surface having a major axis, $2a_2$, a minor axis, $2b_2$, a focal length $2c_2$, and an eccentricity $e_2$, wherein said $2c_1$ is equal to said $2c_2$, said secondary reflecting surface reflecting a secondary portion of said spherically divergent shock wave pulse to produce said secondary shock wave pulse, said major axis $2a_2$ being greater than said major axis $2a_1$, and said eccentricity $e_1$ being greater than said eccentricity $e_2$, whereby said secondary shock wave pulse is separated in time from said primary shock wave pulse by a time delay with respect to said primary shock wave pulse, said time delay being equal to $(2a_2-2a_1)$ divided by s, said primary and secondary reflecting surfaces having common first and second focal points, said first focal point coinciding with said point shock wave source and said second focal point corresponding with said concretions, whereby said primary shock wave arrives at said secondary focal point and said secondary shock wave pulse arrives at said second focal point after said time delay with respect to said primary shock wave, whereby said concretions are comminuted with reduced tissue injury.

2. A microsecond tandem-pulse shock wave generator as disclosed in claim 1, wherein said time delay is 20 to 400 microseconds.

3. A microsecond tandem-pulse shock wave generator as disclosed in claim 1, wherein said major axis $2a_2$ is 30 to 600 millimeters longer than said major axis $2ahd 1$, where said major axis $2a_1$ is between 20 and 40 centimeters.

4. A microsecond tandem-pulse shock wave generator as disclosed in claim 1, wherein said point shock wave source is electrohydraulic.

5. A microsecond tandem-pulse shock wave generator for comminuting, with reduced tissue injury, concretions in vivo, said microsecond tandem-pulse shock wave generator generating a primary shock wave pulse and also generating a secondary shock wave pulse separated in time from said primary shock wave pulse by a primary time delay with respect to said primary shock wave pulse, said microsecond tandem-pulse shock wave generator comprising:

a point shock wave source for producing a spherically divergent shock wave pulse having a speed in water, s, and;

a primary truncated ellipsoidal reflecting surface having a major axis, $2a_1$, a minor axis, $2b_1$, a focal length $2c_1$, and an eccentricity $e_1$, said primary reflecting surface reflecting a primary portion of said spherically divergent shock wave pulse, and;

a secondary reflecting surface consisting of a plurality of n truncated ellipsoidal reflecting surfaces each having a major axis, $2a_n$, a minor axis, $2b_n$, a focal length $2c_n$, and an eccentricity $e_n$, said $2c_1$ is equal to said $2c_n$, said secondary reflecting surfaces reflecting secondary portions of said spherically divergent shock wave pulse to produce said secondary shock wave pulse, each said truncated ellipsoidal reflecting surface being separated from every other by a secondary time delay, said major axes $2a_n$ being greater than said major axis $2a_1$, and said eccentricity $e_1$ being greater than each said eccentricity $e_n$, and each said major axis $2a_n$ being greater than each said major axis $2a_{n-1}$ and each said eccentricity $e_{n-1}$ being greater than each said eccentricity $e_n$, where said n is an integer greater than 1, whereby said secondary shock wave pulse is separated in time from said primary shock wave pulse by a time delay with respect to said primary shock wave pulse, said time delay being equal to $(2a_n-2a_1)$ divided by s, said primary and secondary reflecting surfaces having common first and second focal points, said focal point coinciding with said point shock wave source and said second focal point corresponding with said concretions, whereby said primary shock wave arrives at said second focal point and said secondary shock wave pulse arrives at said second focal point after said primary time delay with respect to said primary shock wave, whereby said concretions are comminuted with reduced tissue injury.

6. A microsecond tandem-pulse shock wave generator as disclosed in claim 5, wherein said primary time delay is 20 to 400 microseconds, and said secondary time delay is 0.5 to 5 microseconds, said secondary shock wave pulse is primarily compressive, and said secondary shock wave pulse collapses said cavitation bubble cluster produced by said primary shock wave pulse.

7. A microsecond tandem-pulse shock wave generator as disclosed in claim 5, wherein said major axes, $2a_n$, are each at least 30 to 600 millimeters longer than said major axis $2a_1$, and each said major axis $2a_n$ is 0.75 to 7.5 millimeters longer than each said major axis $2a_{n-1}$, where said major axis $2a_1$ is between 20 and 40 centimeters.

* * * * *